United States Patent [19]

Chan et al.

[11] Patent Number: 5,034,413

[45] Date of Patent: Jul. 23, 1991

[54] INTRAOCULAR PRESSURE REDUCING 9,11-DIACYL PROSTAGLANDINS

[75] Inventors: Ming F. Chan, Santa Ana; Charles Gluchowski, Mission Viejo; David F. Woodward, El Toro, all of Calif.

[73] Assignee: Allergan, Inc., Irvine, Calif.

[21] Appl. No.: 585,284

[22] Filed: Sep. 18, 1990

Related U.S. Application Data

[63] Continuation of Ser. No. 385,834, Jul. 27, 1989, abandoned.

[51] Int. Cl.$^5$ ............... A61K 31/215; A61K 31/235
[52] U.S. Cl. .................... 514/530; 514/533; 514/913
[58] Field of Search ............ 514/530, 533, 913

[56] References Cited

U.S. PATENT DOCUMENTS 4,060,540 11/1977 Bernady et al. ............... 556/441
4,599,353 7/1986 Bito ............................. 514/530

FOREIGN PATENT DOCUMENTS 8806448 7/1988 PCT Int'l Appl. .
8903384 4/1989 Sweden .

OTHER PUBLICATIONS

Starr, *Exp. Eye Res.* 11, 170–177 (1971).
Zajacz et al., *The Eye: Reproduction, Obstetrics and Gynecology* 4, 316 (1976).
Keun Kim *Investigative Ophthalmology* 14, 36 (1975).
Camras et al., *Invest. Ophthalmol. Visual Sci.* 16, 1125 (1977).
Woodward et al., *Invest. Ophthalmol. Visual Sc.* 30, 1838 (1989).
Nilsson et al., *Exp. Eye Res.* 48, 707 (1989).
Bito, *Arch. Ophthalmol.* 105, 1036 (1987).
Siebold et al., *Prodrug* 5, 3 (1989).

*Primary Examiner*—Frederick E. Waddell
*Assistant Examiner*—Zohreh A. Fay
*Attorney, Agent, or Firm*—Martin A. Voet; Robert J. Baran

[57] ABSTRACT

Certain 9,11-diacyl prostaglandins and their use for lowering intraocular pressure are disclosed herein.

33 Claims, No Drawings

INTRAOCULAR PRESSURE REDUCING 9,11-DIACYL PROSTAGLANDINS

This application is a continuation of application Ser. No. 07/385,834, filed Jul. 27, 1989, now abandoned.

BACKGROUND OF THE INVENTION

The present invention relates to a means for reducing or maintaining intraocular pressure. More particularly it relates to a method and composition for reducing or maintaining intraocular pressure involving the administration of a composition containing a 9,11-diacyl prostaglandin in an ophthalmically acceptable carrier.

The method and compositions of the present invention are particularly useful for the management of glaucoma, a disease of the eye characterized by increased intraocular pressure. On the basis of its etiology, glaucoma has been classified as primary or secondary. For example, primary glaucoma in adults, congenital glaucoma, may be either chronic open-angle or acute or chronic angle-closure. Secondary glaucoma results from pre-existing ocular diseases such as uveitis, intraocular tumor or an enlarged cataract.

The underlying causes of primary glaucoma are not yet well known. The increased intraocular tension is due to obstruction of aqueous humor outflow. In chronic open-angle glaucoma, the anterior chamber and its anatomic structures appear normal, but drainage of the aqueous humor is impeded. In acute and chronic angle-closure glaucoma, the anterior chamber is shallow, the filtration angle is narrowed and the iris may obstruct the trabecular meshwork at the entrance to the canal of Schlemm. Dilation of the pupil may push the root of the iris forward against the angle or may produce pupillary block and thus precipitate an acute attack. Eyes with narrow anterior chamber angles are predisposed to acute angle-closure glaucoma attacks of varying degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occulsion, trauma to the eye, operative procedures and intraocular hemorrhage.

Considering all types together, glaucoma occurs in about 2% of all persons over the age of 40 and may be asymptomatic for years before progressing to rapid loss of vision. In cases where surgery is not indicated, topical $\beta$-adrenoceptor antagonists have traditionally been the drugs of choice for treating glaucoma.

Carbon-1 esters of certain prostaglandins, have been reported to possess ocular hypotensive activity. However, prostaglandin ocular hypotensives generally suffer from the disadvantage of inducing conjunctival hyperemia of varying severity and duration, smarting, and foreign body sensation, as well as presenting solubility problems in certain ophthalmically advantageous carriers.

This invention relates to derivatives of the known prostaglandins formulated in a pharmaceutically acceptable vehicle, and ophthalmic use of those prostaglandins. The present invention is advantageous with respect to the prior art by virtue of the reduction of the aforementioned undesirable side effects with retention of ocular hypotensive activity.

SUMMARY OF THE INVENTION

In accordance with one aspect of the present invention, there is provided a method of treating ocular hypertension which comprises applying to the eye an amount sufficient to treate ocular hypertension of an 9,11-diacyl prostaglandin, the compounds of formula I.

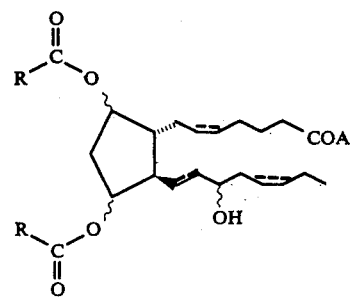

In formula I, the dashed bond represents a single bond or a double bond which can be in the cis or trans configuration; A is —OH, or a pharmaceutically acceptable salt thereof or —OR$_1$ where R$_1$ is lower alkyl; the two R groups are independently an acyclic hydrocarbon, saturated or unsaturated, having from 1 to 20 carbon atoms, or R is —(CH$_2$)$_n$R$_2$ where n is 0–10 and R$_2$ is an aliphatic hydrocarbon ring or an aromatic or heteroaromatic ring.

In accordance with another aspect of the present invention, there is provided an ophthalmically acceptable composition for reducing ocular hypertension which comprises at least one 9,11-diacyl prostaglandin described above, present in an ophthalmically acceptable excipient for topical application to the surface of the eye. Such an excipient is one which does not have a deleterious or untoward effect on the eye when used in normal treatment regimens.

Further features and advantages of the present invention will become apparent from the detailed description of the invention, taken together with the illustrative examples.

DETAILED DESCRIPTION OF THE INVENTION

It has been discovered that certain prostaglandins lower intraocular pressure in man and other mammals when applied topically to the eye. Although the precise mechanism is not yet known, prostaglandins appear to increase aqueous humor outflow to restore a normotensive or hypotensive state. However, topical application of prostaglandins generally causes side effects such as conjunctival hyperemia, smarting and foreign body sensation which range in degree from undesirable to unacceptable, depending upon the particular patient and dosage necessary to produce a sufficient pressure regulating effect. In accordance with one aspect of the present invention, there has been provided a method for treating ocular hypertension which comprises administering to the eye a compound of formula I. It has further been discovered that these esters which may be more effective than PGF$_{2\alpha}$ both in terms of degree and duration of activity. In addition, animals treated with formulations comprising these esters experience significantly reduced adverse side effects, notably ocular surface hyperemia, compared to that reported for PGF$_{2\alpha}$ and PGF$_{2\alpha}$-1-isopropyl ester.

In the foregoing illustration, as well as those provided hereinafter, wavy line attachments indicate either the alpha ($\alpha$) or beta ($\beta$) configuration. The dotted lines on bonds between carbons 5 and 6 (C-5), between carbons 13 and 14 (C-13), and between carbons 17 and 18 (C-17) indicate a single or double bond which can be in the cis or trans configuration. If two solid lines are used at C-5, C-13, or C-17, it indicates a specific configuration for that double bond. Hatched lines used at position C-9, C-11 and C-15 indicate the $\alpha$ configuration. If one were to draw the $\beta$ configuration, a solid triangular line would be used at any of these three positions.

The naturally occurring stereochemistry of PGF$_{2\alpha}$ includes the C-9, C-11 and C-15 position hydroxyl groups in the $\alpha$ configuration. In the compositions of the present invention, however, esters of prostaglandins having the C-9 or C-11 or C-15 hydroxyl group in the $\beta$ configuration are also contemplated.

The 9,11-diacyl prostaglandins suitable for use in this invention can comprise any of a variety of acyl substituents at the 9 and 11 positions. As per formulas I, either R group can be an aliphatic acyclic hydrocarbon having from one to twenty carbon atoms, inclusive. Preferably each R group has from one to ten carbon atoms. Most preferably each R group is the same and is methyl, ethyl, propyl, butyl, pentyl, or an isomeric form thereof. The prefered isomeric forms are the isopropyl, butyl, isobutyl, and t-butyl isomers.

Alternatively each R group can comprise a cyclic component. In particular, either R group can be (CH$_2$)$_n$R$_2$ where n is 0–10 and R$_2$ is a saturated or unsaturated ring, preferably a saturated ring having from three to seven carbon atoms, inclusive, or an aromatic or heteroaromatic ring of 5 to 7 carbon atoms, and having oxygen, nitrogen or sulfur in the case of a heteroaromatic ring. Preferably n is 0–4.

In all formulations provided herein broken line attachments to the cyclopentane ring indicate substituents in the $\alpha$ configuration. Thickened solid line attachments to the cyclopentane ring indicate substituents in the $\beta$ configuration. For instance, PGF$_{6_2}$ compounds have the same structure as the above PGF$_\alpha$ compounds, except that the hydroxyl at the C-9 position is in the $\beta$ configuration. Also, the broken line attachment of the hydroxyl group to the C-15 carbon atom signifies the $\alpha$ configuration; therefore, compounds with the epi configuration for the hydroxyl group at C-15 are designated by using 15$\beta$ and if there is no indication of the $\beta$ configuration, the configuration is the $\alpha$ form.

The preferred compounds of this invention are those which have the following structures.

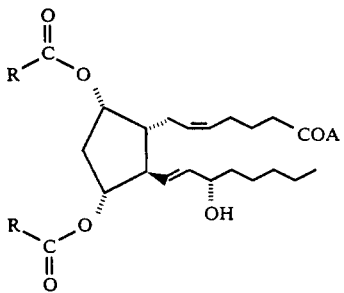

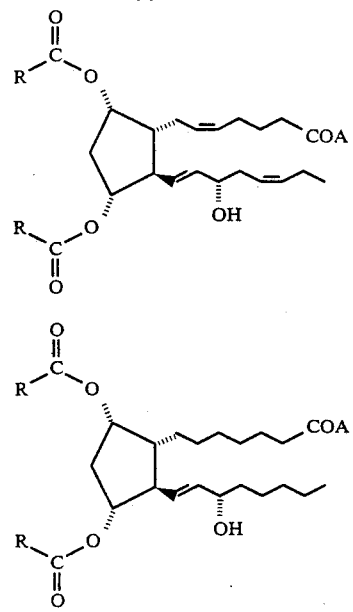

Within this preferred group, the most preferred compounds are those where both R groups are the same and are methyl, isopropyl, butyl, isobutyl, and t-butyl.

Where A is —OH the acid can be converted to a salt O$^-$X$^+$ where X$^+$ is the cation component of any of a variety of pharmaceutically acceptable salts. A pharmaceutically acceptable salt may be prepared for any compound in this disclosure having a functionality capable of forming such a salt, in particular, the carboxylic acid group at C$_1$ of the 9,11-diacyl prostaglandins disclosed herein. A pharmaceutically acceptable salt is any salt which retains the activity of the parent compound and does not impart any deleterious or undesirable effect on the subject to which it is administered and in the context in which it is administered.

A pharmaceutically acceptable salt of an acid may be derived from an organic or inorganic base. Such a salt may be a mono- or polyvalent ion. Of particular interest are the inorganic ions, sodium, potassium, calcium, magnesium and zinc. Organic ammonium salts may be made with amines, such as mono-, di-, and trialkyl amines or ethanol-amines. Salts may also be formed with caffeine, tromethamine and similar molecules.

In another aspect, this invention relates to a composition which can be applied topically to the eye to lower intraocular pressure. This composition comprises one or more of the foregoing 9,11-diacyl prostaglandins therein. The composition may comprise any of a variety of ophthalmically acceptable carriers as will be known to those skilled in the art of ocular drug delivery. A preferred method of application would be topically, in a pharmaceutically acceptable topical formulation. Such a carrier may be comprised of a saline and/or detergent, containing pharmaceutically required or advantageous adjuvants, along with an effective dose of the intraocular pressure reducing drug.

In accordance with a preferred embodiment of the present invention, the carrier comprises a solution having polysorbate 80–10 mM TRIS in the range of from about 0.05–1.0% by weight, and preferably about 0.1%, which is particularly suited for administration in the form of a liquid eye drop. This carrier may additionally comprise pharmaceutically advantageous adjuvants such as a preservative, antibiotic/antimycotic agents, pH buffers or osmotic balancers. In a preferred embodiment of the present invention, the intraocular pressure-reducing agent comprises a derivative of $PGF_{2\alpha}$, preferably one or a combination of the 9,11-diacyl, 9,11-diisobutyryl, 9,11-isovaleryl or 9,11-dipivaloyl derivatives of $PGF_{2\alpha}$.

The optimal concentration of the prostaglandin derivative is a function of a variety of factors, such as desired frequency of application and duration of effect, level of adverse side effects and considerations implicated by the chemical nature of the carrier. In general, however, concentrations are contemplated within the range of from about 0.0001% to 1%, preferably from 0.001% to 0.1% by weight in relation to the pharmaceutically acceptable carrier.

The following examples are set out to illustrate, but not limit, the scope of this invention. All temperatures are in degrees centigrade.

EXAMPLE 1

Preparation of $PGF_{2\alpha}$15-t-butyldimethylsilyl ether $PGF_{2\alpha}$ (69.6 mg, 0.197 mmol) and 1-butaneboronic acid (22 mg, 0.22 mmol) were heated under reflux in dichloromethane (1 ml) for 20 min. under argon. The solvent was removed under reduced pressure and the residue was kept under high vacuum for 2 hours.

The residue from the preceeding step was taken up in dry dichloromethane (0.5 ml) and cooled to 0°. 2,6-Lutidine (69 μl, 0.59 mmol) and t-butyldimethylsilyl trifluoromethanesulfonate (113 μl, 0.49 mmol) were added with stirring. The ice bath was removed and the solution was stirred at 25° for 2 hours. New batches of 2,6-lutidine and t-butyldimethylsilyl trifluoromethanesulfonate were added and stirring was continued for a further 5 hours. The reaction mixture was diluted with dichloromethane and was washed with 10% citric acid and brine. The organic layer was dried over anhydrous sodium sulfate and concentrated in vacuo. The residual oil was dissolved in methanol (1 ml) and stirred for 2 hours at 25°. Evaporation of solvent gave the crude $PGF_{2\alpha}$15-t-butyldimethylsilyl ether.

$^1$H NMR (300 MHz, $CDCl_3$): δ 0.01 (3H, s), 0.02 (3H, s), 0.86 (12H, large singlet with signals underneath), 1.2–2.4 (20H, m), 3.97 (1H, distorted quintet, J=4 Hz), 4.05 (1H, q, J=6.2 Hz), 4.19 (1H, t, J=4.5 Hz), 5.3–5.4 (2H, m), 5.40 and 5.52 ppm (2H, ABX, J=15.4, 8.4 and 5.9 Hz).

EXAMPLE 2

Preparation of 9,11-acetyl $PGF_{2\alpha}$

The crude silyl ether prepared in Example 1 above was treated at 0° with pyridine (0.75 ml), acetic anhydride (99 μl, 0.89 mmol) and 4-dimethylaminopyridine (2 mg, 0.16 mmol). The solution was stirred at 0° for 3 hours. The solvents were removed in vacuo and the residue was taken up in ethyl acetate. The organic phase was washed with 10% citric acid and brine, dried over anhydrous magnesium sulfate and concentrated to give a light yellow oil. Purification by silica gel column chromatography (30% ethyl acetate in hexanes with 0.5% acetic acid as eluent) gave the 9,11-diacetyl $PGF_{2\alpha}$15-t-butyldimethylsilyl ether.

The diacetyl silyl ether (80 mg, 0.144 mmol) was stirred vigourously in 80% aqueous acetic acid (1 ml) at 25° for 14 hours. The solvents were evaporated in vacuo to leave a colorless oil which was purified by column chromatography (silica gel, 35–40% ethyl acetate in hexanes with 0.5% acetic acid) to give the 9,11-diacetyl $PGF_{2\alpha}$.

Spectral Data $^1$H NMR (300 MHz, $CDCl_3$): δ 0.85 (3H, t, J=6 Hz), 1.2–2.3 (12H, m), 2.01 (3H, s), 2.06 (3H, s), 2.30 (2H, t, J=6.3 Hz), 2.45–2.6 (2H, m), 4.15 (1H, q, J=6 Hz), 4.89 (1H, dt, J=8, 4.5 Hz), 5.10 (1H, t, J=4.5 Hz), 5.3–5.4 (2H, tight AB), 5.52 and 5.6 ppm (2H, ABX J=15, 7.7 and 5.8 Hz).

$^{13}$C NMR (75 MHz, $CDCl_3$): δ 13.96, 21.06, 21.17 22.56, 24.41, 24.48, 24.96, 26.22, 31.67, 32.90, 36.85, 38.88, 47.89, 51.91, 72.26, 74.05, 77.85, 127.98, 129.88, 129.93, 135.38, 170.53, 170.85 and 177.55 ppm.

IR (film): 2400–3600, 2930, 2860, 1710, 1430, 1370, 1250, 1040, 1025, 970, 915 and 735 $cm^{-1}$.

MS (EI on 15-trimethylsilyl ether methyl ester): m/z 524 (1.4, M+), 393(26), 333(100), 332(17), 314(12), 199(13), 117(13), 75(15) and 73(33).

EXAMPLE 3

Preparation of 9,11-diisobutryl $PGF_{2\alpha}$

Crude silyl ether prepared in Example 1 was treated at 0° with pyridine (0.7 ml), isobutyric anhydride (135 μl, 0.81 mmol) and 4-dimethylaminopyridine (2 mg, 0.02 mmol). The solution was stirred at 25° for 16 hours. Solvents were removed in vacuo and the residue was taken up in ethyl acetate. The organic phase was washed with 10% citric acid and brine, dried over anhydrous magnesium sulfate and concentrated to give a light yellow oil. Purification by flash chromatography ($SiO_2$, 20% ethyl acetate/hexane) gave 9,11-diisobutyryl $PGF_{2\alpha}$15-t-butyldimethylsilyl ether.

The diisobutyryl silyl ether (89 mg, 0.128 mmol) was stirred vigorously in 80% aqueous acetic acid (0.3 ml) at 25° for 18 hours. The solvents were evaporated in vacuo leaving a colorless oil which was purified via column chromatography producing the 9,11-diisobutyryl $PGF_{2\alpha}$.

Spectral Data $^1$H NMR (300 MHz, $CDCl_3$): δ 0.85 (3H, t, J=6 Hz), 1.11 (6H, dd, J=2.8, 7.1 Hz) 1.16 (6H, d, J=7 Hz), 1.2–2.3 (18H, m), 2.4–2.6 (2H, m), 2.29 (2H, t, J=6.5 Hz), 4.16 (1H, distorted q, J=4 Hz), 4.92 (1H, ddd, J=4, 7.5 and 9 Hz), 5.13 (1H, t, J=4.5 Hz), 5.3–5.45 (2H, tight AB) and 5.55–5.65 ppm (2H, tight AB).

$^{13}$C NMR (75 MHz, $CDCl_3$): δ 13.98, 18.76, 18.87, 22.55, 24.42, 24.95, 26.16, 31.67, 32.80, 33.86, 34.22, 36.89, 39.05, 48.32, 52.27, 72.21, 73.74, 127.96, 129.89, 129.94, 134.97, 176.34, 176.84 and 177.27 ppm.

IR (film): 2400–3600, 2960, 2920, 2860, 1710, 1455, 1382, 1332, 1290, 1250, 1190, 1150, 1070, 1010, 965, 915, 845 and 730 $cm^{-1}$.

MS (EI on 15-trimethylsilyl ether methyl ester): m/z 581 (1, M+), 421(17), 334(26), 333(100), 332(12), 199(13), 145(12), 75(16), 73(37) and 71(23).

EXAMPLE 4

Preparation of 9,11-diisolvaleryl $PGF_{2\alpha}$

Crude silyl ether (52.5 mg, 0.112 mmol) prepared as per Example 1 was treated at 0° with pyridine (0.7 ml), isovaleric chloride (34 μl, 0.28 mmol) and 4-dimethylaminopyridine (1.21 mg, 0.01 mmol). The solution was stirred at 0° for 6 hours. Then solvents were removed in vacuo and the residue was taken up in ethyl acetate (5 ml). The organic phase was washed with 2×5 ml water, followed by brine and then dried over anhydrous sodium sulfate and concentrated in vacuo. Purification by flash chromatography yielded the 9,11-diisovaleryl $PGF_{2\alpha}$ 15-t-butyldimethylsilyl ether.

Combined diisovalerate silyl ether batches as prepared above (63 mg) were stirred vigorously in 80% aqueous acetic acid (1 ml) at 25° for 16 hours. The solvents were evaporated in vacuo and taken up in 5 ml ethyl acetate. The ethyl acetate solution was then washed with 2×7 ml water followed by 7 ml of brine. The ethyl acetate layer was dried over sodium sulfate and concentrated to yield the crude diisovaleryl derivative. It was purified further by reverse phase thin layer chromatography (7:1 $CH_2Cl_2$, MeOH; 7:3 MeOH, $H_2O$) to give the 9,11-diisovaleryl $PGF_{2\alpha}$.

Spectral Data $^1H$ NMR (300 MHz, $CDCl_3$): δ0.87 (3H, partially hidden t, J=6 Hz), 0.93 (6H d, J=6.5 Hz), 0.97 (6H, d, J=6.5 Hz), 1.2–2.35 (20H m), 2.31 (2H, t, J=5.2 Hz), 2.5–2.6 (2H, m), 4.22 (1H, m), 4.96 (1H, m), 5.19 (1H, t, J=4.9 Hz), 5.3–5.5 (2H, m), 5.55–5.65 ppm (2H, tight AB).

$^{13}C$ NMR (75 MHz, $CDCl_3$): δ14.02, 22.35, 22.57, 24.37, 24.46, 25.01, 25.53, 25.77, 25.89, 26.09, 31.68, 32.69, 36.98, 39.21, 43.47, 43.69, 48.29, 52.13, 72.26, 73.81, 77.21, 77.54, 127.98, 129.83, 129.91, 134.74, 172.54, 172.84 and 176.68 ppm.

MS (EI on 15-trimethylsilyl ether methyl ester): m/z 608(0.7, M+) 435(11), 423(11), 334(20), 333(76), 332(14), 319(18), 314(10), 199(18), 167(22), 159(19), 149(53), 129(16), 113(11), 99(13), 91(11), 85(41), 83(17), 81(21), 77(31), 75(35), 74(13), 73(80), 71(37), 70(16), 69(29), 58(10), 57(100), 56(11) and 55(31).

The foregoing procedures can be modified to produce all the 9,11-diacyl $PGF_{2\alpha}$ compounds of this invention as will be appreciated by one of skill in the art.

EXAMPLE 5

Intraocular Pressure Reducing Effect in Rabbits

Experimental quantities of the designated 9,11-diacyl prostaglandins prepared in accordance with the procedure of Example 1–4 were tested as follows. The resulting 9,11-diacyl $PGF_{2\alpha}$ derivatives were added to a polysorbate carrier in amounts to produce a 0.01%, 0.1% or 1% solution of each ester. A group of 8 experimental rabbits was treated by administering approximately one drop of each solution to the surface of the eye, and intraocular pressure was measured by applanation pneumatonometry (Model 30 RT manufactured by Digilab) at the time of administration and at intervals of 2, 3, 4, 6, 8 or 10 hours thereafter. The following data were obtained:

TABLE I

INTRAOCULAR PRESSURE DECREASES AT PREDETERMINED TIMES (HR) AFTER PROSTAGLANDIN ADMINISTRATION

| Compound | PG Dose % | Time (Hours) | | | | | |
|---|---|---|---|---|---|---|---|
| | | 2 | 3 | 4 | 6 | 8 | 10 |
| Reduction in IOP (mm Hg) | | | | | | | |
| $PGF_{2\alpha}$-1-isopropyl ester | 0.01% | — | — | 1.3 | 5.8[2] | 3.5[2] | 2.9[2] |
| | 0.1% | — | — | 3.2[1] | 9.7[2] | 10.1[2] | 10.0[2] |
| 9,11-diacetyl $PGF_{2\alpha}$ | 0.01% | 2.6[2] | 3.4[2] | 3.6[1] | 5.7[1] | — | — |
| | 0.1% | 2.3 | 2.7[1] | 4.6[2] | 3.7[1] | — | — |
| 9,11-diisobutyryl $PGF_{2\alpha}$ | 0.01% | 3.1[2] | 3.6[2] | 1.8[1] | 0.1 | — | — |
| | 0.1% | 0 | 0.9 | 0 | 1.5[2] | 1.1 | 0.7 |
| 9,11-diisovaleryl $PGF_{2\alpha}$ | 0.1% | 1.9 | 4.8[2] | 4.7[2] | 4.7[2] | 3.3[1] | — |
| 9,11-dipivaloyl $PGF_{2\alpha}$ | 0.1% | 2.3 | 2.1 | 1.5 | 0 | — | — |
| | 1.0% | 0.3 | 3.7 | 4.2[1] | 5.7[2] | 5.5[2] | 3.2[1] |
| Percent Animal Exhibiting Ocular Surface Hyperemia | | | | | | | |
| $PGF_{2\alpha}$-1-isopropyl ester | 0.01% | 100 | 100 | 100 | 100 | 100 | 100 |
| | 1.0% | 100 | 100 | 100 | 100 | 100 | 87.5 |
| 9,11-diacetyl $PGF_{2\alpha}$ | 0.01% | 100 | 100 | 100 | 20 | — | — |
| | 0.1% | 100 | 100 | 100 | 100 | — | — |
| 9,11-diisobutyryl $PGF_{2\alpha}$ | 0.01% | 100 | 100 | 87.5 | 37.5 | — | — |
| | 0.1% | 100 | 100 | 100 | 100 | 37.5 | 0 |
| 9,11-diisovaleryl $PGF_{2\alpha}$ | 0.1% | 100 | 100 | 100 | 100 | 62.5 | — |
| 9,11-dipivaloyl $PGF_{2\alpha}$ | 0.1% | 0 | 0 | 0 | 0 | — | — |
| | 1.0% | 63 | 63 | 63 | 63 | 0 | 0 |

1 — $p < 0.05$; 2 — $p < 0.01$

Although this invention has been described in terms of certain preferred embodiments, other embodiments that are apparent to those of ordinary skill in the art are also within the scope of this invention. These embodiments are set out to illustrate the invention, not to limit it.

What is claimed:

1. A method of treating ocular hypertension which comprises applying to the eye in an ophthalmically acceptable excipient an amount sufficient to treat ocular hypertension of the compound:

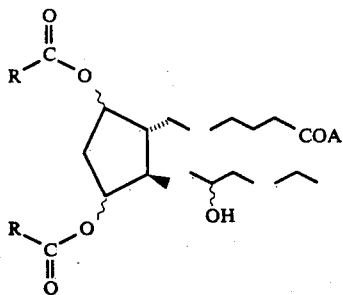

wherein the dashed bond represents a single bond, or a double bond which can be in the cis or trans configuration; A is —OH, or a pharmaceutically acceptable salt thereof or —OR$_1$ where R$_1$ is lower alkyl; the two R groups are independently an acyclic hydrocarbon, saturated or unsaturated, having from 1 to 20 carbon atoms, or R is —(CH$_2$)$_n$R$_2$ where n is 0–10 and R$_2$ is an aliphatic hydrocarbon ring, or an aromatic ring.

2. The method of claim 1 wherein the R groups are the same and are methyl, ethyl, propyl, butyl, pentyl or an isomeric form thereof.

3. The method of claim 2 where the C-5 and C-13 bonds are cis and trans double bonds respectively, the C-17 bond is a single bond, and the C-9, C-11 and C-15 substituents are in the α configuration, the compound having the following formula:

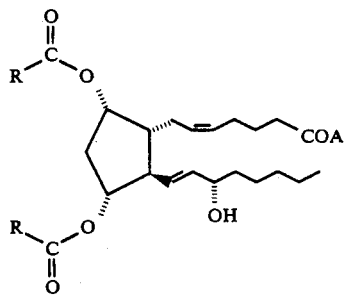

4. The method of claim 3 where the R groups are methyl, the diacetyl compound.

5. The method of claim 3 where the R groups are —CH(CH$_3$)$_2$, the diisobutyryl compound.

6. The method of claim 3 where the R groups are —CH$_2$CH(CH$_3$)$_2$, the diisovaleryl compound.

7. The method of claim 3 where the R groups are —C(CH$_3$)$_3$, the dipivaloyl compound.

8. The method of claim 1 where C-5 and C-17 are cis double bonds, C-13 a trans double bond, and the substituents at C-9, C-11 and C-15 are in the α configuration, the compound of the following formula.

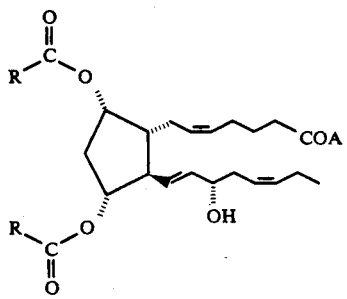

9. The method of claim 8 wherein the R groups are the same and are methyl, ethyl, propyl, butyl, pentyl or an isomeric form thereof.

10. The method of claim 1 where the C-5 and C-17 bonds are single bonds, the C-13 bond is a trans double bond, and the substituents at C-9, C-11 and C-15 are in the α configuration, the compound of the following formula.

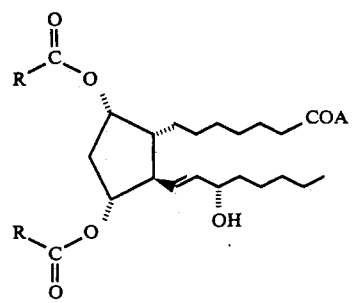

11. The method of claim 10 wherein the R groups are the same and are methyl, ethyl, propyl, butyl, pentyl or an isomeric form thereof.

12. An ophthalmically acceptable composition for reducing ocular hypertension which comprises an ophthalmically acceptable excipient and an amount sufficient to treat ocular hypertension of at least one compound of the formula:

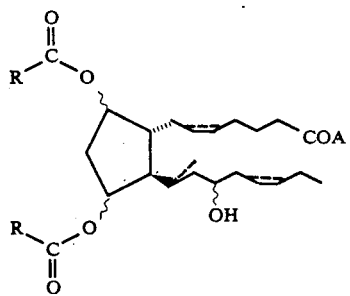

wherein the dashed bond represents a single bond, or a double bond which can be in the cis or trans configuration; A is —OH, or a pharmaceutically acceptable salt thereof or —OR$_1$ where R$_1$ is lower alkyl; the two R groups are independently an acyclic hydrocarbon, saturated or unsaturated, having from 1 to 20 carbon atoms, or R is —(CH$_2$)$_n$R$_2$ where n is 0–10 and R$_2$ is an aliphatic hydrocarbon ring, or an aromatic ring.

13. The composition of claim 12 wherein the R groups are the same and are methyl, ethyl, propyl, butyl, pentyl or an isomeric form thereof.

14. The composition of claim 13 where the C-5 and C-13 bonds are cis and trans double bonds respectively, the C-17 bond is a single bond, and the substituents at C-9, C-11 and C-15 are in the α configuration, the compound having the following formula.

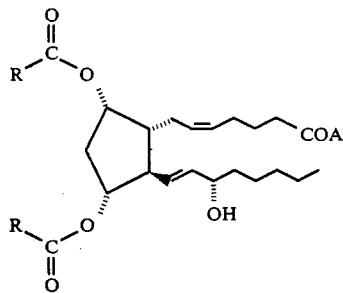

15. The composition of claim 14 where the R groups are methyl, the diacetyl compound.

16. The composition of claim 14 where the R groups are —CH(CH₃)₂, the diisobutyryl compound.

17. The composition of claim 14 where the R groups are —CH₂CH(CH₃)₂, the diisovaleryl compound.

18. The composition of claim 14 where the R groups are —C(CH₃)₃, the dipivaloyl compound.

19. The composition of claim 12 where C-5 and C-17 bonds are cis double bonds, C-13 is a trans double bond, and the substituents at C-9, C-11 and C-15 are in the α configuration, the compound of the following formula.

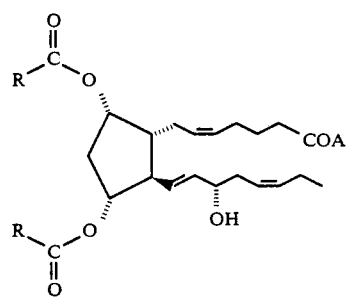

20. The composition of claim 19 wherein the R groups are the same and are methyl, ethyl, propyl, butyl, pentyl or an isomeric form thereof.

21. The composition of claim 12 where the C-5 bond and the C-17 bond are single bonds, C-13 is a trans double bond, and the substituents at C-9, C-11 and C-15 are in the α configuration, the compound of the following formula.

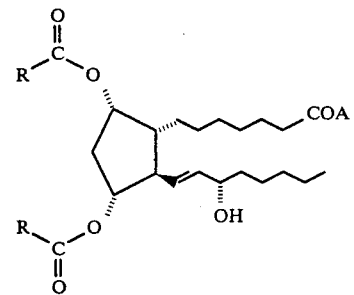

22. The composition of claim 20 wherein the R groups are the same and are methyl, ethyl, propyl, butyl, pentyl or an isomeric form thereof.

23. A pharmaceutical composition which comprises an effective dose of a compound of the formula

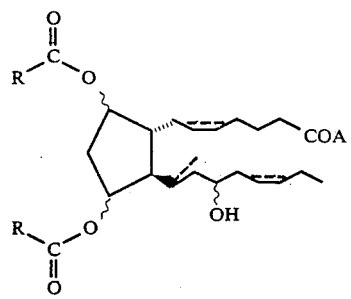

wherein the dashed bond represents a single bond, or a double bond which can be in the cis or trans configuration; A is —OH, or a pharmaceutically acceptable salt thereof or —OR₁ where R₁ is lower alkyl; the two R groups are independently acyclic hydrocarbon, saturated or unsaturated, having from 1 to 20 carbon atoms, or R is —(CH₂)ₙR₂ where n is 0–10 and R₂ is an aliphatic hydrocarbon ring, or an aromatic ring, in admixture with a pharmaceutically acceptable carrier.

24. The composition of claim 23 wherein the R groups are the same and are methyl, ethyl, propyl, butyl, pentyl or an isomeric form thereof.

25. The composition of claim 24 wherein the C-5 and C-13 bonds are cis and trans double bonds respectively, the C-17 bond is a single bond, and the C-9, C-11 and C-15 substituents are in the α configuration, the compound having the following formula:

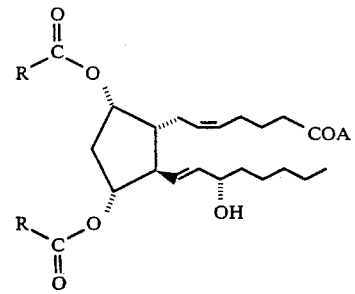

26. The composition of claim 25 wherein the R groups are methyl, the diacetyl compound.

27. The composition of claim 25 wherein the R groups are —CH(CH₃)₂, the diisobutyryl compound.

28. The composition of claim 25 wherein the R groups are —CH₂CH(CH₃)₂, the diisovaleryl compound.

29. The composition of claim 25 wherein the R groups are —CH(CH₃)₃, the dipivaloyl compound.

30. The composition of claim 23 wherein C-5 and C-17 are cis double bonds, C-13 is a trans double bond, and the substituents at C-9, C-11 and C-15 are in the α configuration, the compound of the following formula

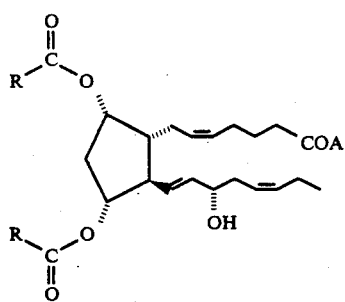

31. The composition of claim 30 wherein the R groups are the same and are methyl, ethyl, propyl, butyl, pentyl or an isomeric form thereof.

32. The composition of claim 23 wherein the C-5 and C-17 bonds are single bonds, the C-13 bond is a trans double bond, and the substituents at C-9, C-11 and C-15 are in the α configuration, the compound of the following formula

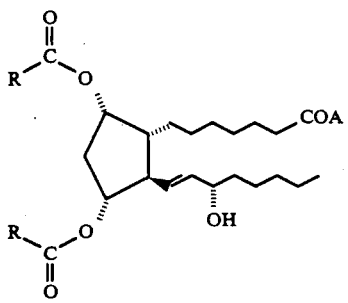

33. The composition of claim 32 wherein the R groups are the same and are methyl, ethyl, propyl, butyl, pentyl or an isomeric form thereof.

* * * * *